(12) United States Patent
Marek et al.

(10) Patent No.: US 7,141,090 B2
(45) Date of Patent: Nov. 28, 2006

(54) ACTIVE FILTER TEMPERATURE CONTROL

(75) Inventors: Gerald Marek, Ann Arbor, MI (US); Norbert Kreft, Ann Arbor, MI (US)

(73) Assignee: AVL North America Inc., Plymouth, MI (US)

(*) Notice: Subject to any disclaimer, the term of this patent is extended or adjusted under 35 U.S.C. 154(b) by 618 days.

(21) Appl. No.: 10/402,282

(22) Filed: Mar. 28, 2003

(65) Prior Publication Data

US 2004/0191130 A1 Sep. 30, 2004

(51) Int. Cl.
*G01N 1/22* (2006.01)

(52) U.S. Cl. ............... 95/14; 95/23; 96/413; 96/420; 96/422; 73/963.11

(58) Field of Classification Search ............ 96/413, 96/420, 422; 95/14, 17, 18, 23, 283; 73/23.2, 73/863.23, 863.11, 863.12
See application file for complete search history.

(56) References Cited

U.S. PATENT DOCUMENTS

| | | | |
|---|---|---|---|
| 3,841,145 A * | 10/1974 | Boubel | 73/863.03 |
| 3,986,386 A | 10/1976 | Beltzer et al. | |
| 5,052,425 A | 10/1991 | Hohenberg et al. | |
| 6,399,391 B1 * | 6/2002 | Tomlin | 436/123 |
| 2002/0020232 A1 | 2/2002 | Yamagishi et al. | |
| 2003/0110950 A1 * | 6/2003 | Sjostrom et al. | 96/413 |

FOREIGN PATENT DOCUMENTS

| | | |
|---|---|---|
| EP | 0610523 A1 | 8/1994 |
| EP | 1462791 A3 | 11/2004 |
| JP | 2002055029 | 2/2002 |
| JP | 2004301837 | 10/2004 |

* cited by examiner

*Primary Examiner*—Frank M. Lawrence
(74) *Attorney, Agent, or Firm*—Carlson, Gaskey & Olds

(57) ABSTRACT

An emission sampling system includes an exhaust gas probe for sampling exhaust gas. A dilution gas source provides a dilution gas, and a mixing device is in fluid communication with the exhaust gas probe and the dilution gas source to mix the sampled exhaust gas and the dilution gas to form a diluted exhaust gas. A particulate filter is in fluid communication with the mixing device downstream therefrom. A dilution temperature conditioning device is arranged between the dilution gas source and the mixing device for obtaining a desired dilution gas temperature. A temperature sensor is arranged in the sampling system for producing a temperature signal corresponding to a temperature of fluid flowing through the sampling system. A controller is connected to the temperature sensor for processing the temperature signal and determining a filter temperature from the temperature signal. The controller commands the conditioning device in response to the filter temperature.

14 Claims, 2 Drawing Sheets

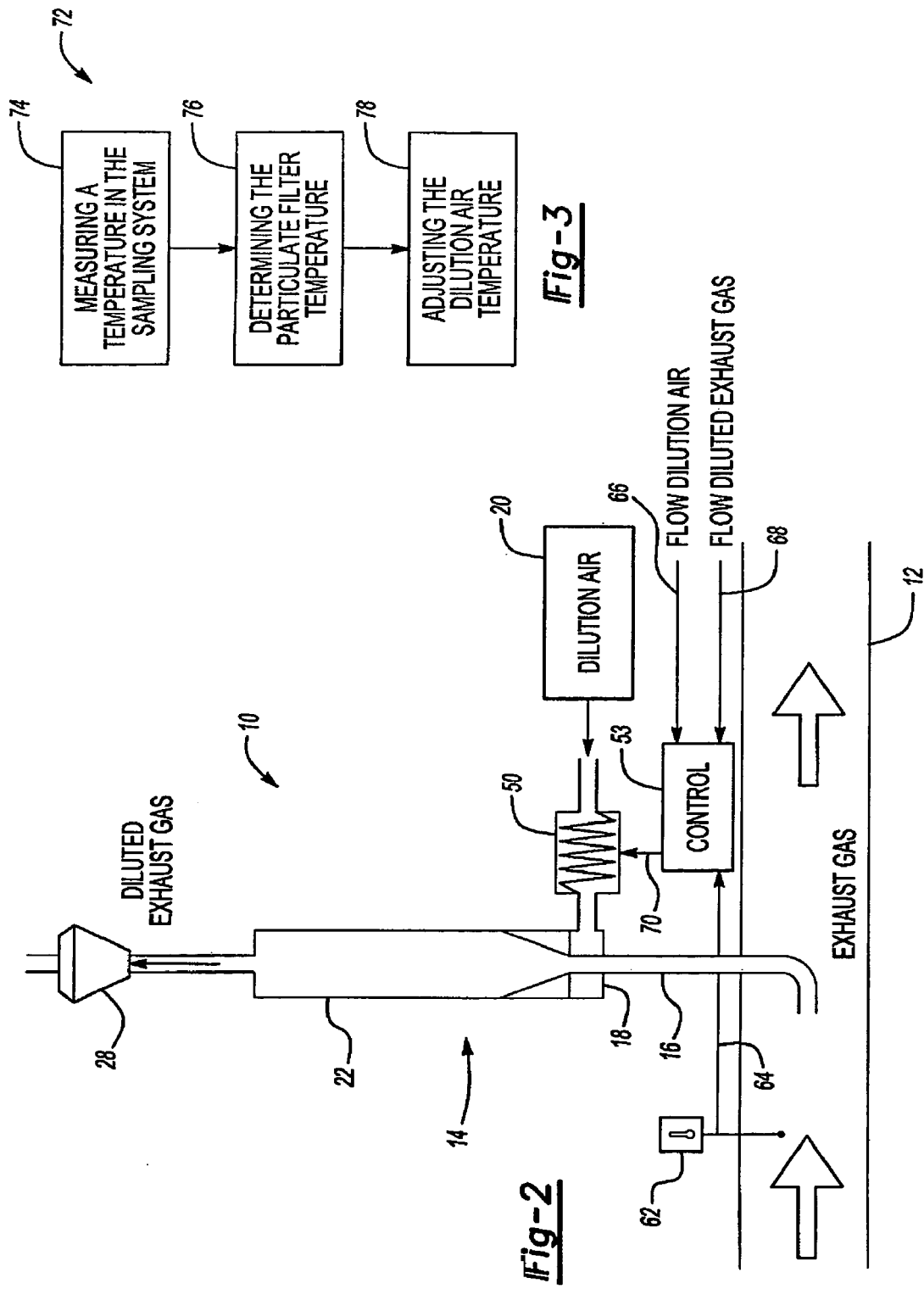

ACTIVE FILTER TEMPERATURE CONTROL

BACKGROUND OF THE INVENTION

This invention relates to an emissions sampling system, and more particularly, the invention relates to an active filter temperature control method and apparatus for controlling the temperature of a particulate filter.

Emissions sampling systems are used to measure the products of combustion of a vehicle engine or other power plant to determine compliance with Federal regulations. Particulate matter is a product of combustion measured using a filter that collects the particulate matter during an emissions sampling test. Typically several filters elements are placed in series with a diluted exhaust gas sample stream to capture the particulate matter. The weight of the empty filter prior to the test is subtracted from the weight of the loaded filter subsequent to the test to determine the particulate matter emitted from the tested power plant.

The temperature at the filter sampling point has been found to strongly influence the accuracy of the test. Particulate test regulations are being adopted that require a tight temperature range at the filter, for example 47° C. Plus or minus 5° C. Some European standards may require the filter temperature to be maintained at 25° C. Plus or minus 5° C. The prior art has attempted to control the temperature in the area of the filter in several ways. For example, the filter temperature is raised to achieve a desired temperature by a heat exchange process in which a length of tubing is heated.

Utilizing a mechanical heat exchanged process for either the sample exhaust gas tubing or the diluted exhaust gas tubing requires a certain amount of surface area to achieve proper heat exchange. However, diffusion losses occur as particulate matter collects on the walls of the tubing. Any particulate matter collected on the walls will not be collected by the filter thereby adversely affecting the accuracy of the test. Accordingly, it is important to reduce the surface area as much as possible to prevent diffusion losses.

In another method, the temperature of the dilution gas is chilled to 15° C. Or some other fixed temperature to lower the temperature in the area of the filter. The fixed temperature of the dilution gas is determined based upon a maximum exhaust gas temperature when combined with the chilled dilution gas would achieve the desired temperature in the area of the filter. However, the temperature in the area of the filter is undesirably low and out of range for other exhaust gas temperature conditions.

Another prior art method to control the temperature in area of the filter is to adjust the portion of dilution gas mixed with the sample of the exhaust gas to change the temperature. However, regulations only permit the dilution ratio to be adjusted a very small amount during the test. Since the dilution ratio must remain somewhat fixed during the test, the dilution ratio must be optimized for one specific exhaust gas temperature, which is typically the maximum exhaust gas temperature. Again, the temperature in the area of the filter is too low for other exhaust gas temperatures during the test.

Therefore, what is needed is an active filter temperature control system and method enabling the temperature in the area of the filter to be maintained within a relatively tight range without adversely affecting the accuracy of the test.

SUMMARY OF THE INVENTION AND ADVANTAGES

The present invention provides an emission sampling system including an exhaust gas probe for sampling exhaust gas. A dilution gas source provides a dilution gas, and a mixing device is in fluid communication with the exhaust gas probe and the dilution gas source to mix the sampled exhaust gas and the dilution gas to form a diluted exhaust gas. A particulate filter is in fluid communication with the mixing device downstream therefrom. A dilution temperature conditioning device is arranged between the dilution gas source and the mixing device for obtaining a desired dilution gas temperature. A temperature sensor is arranged in the sampling system for producing a temperature signal corresponding to a temperature of fluid flowing through the sampling system. In one embodiment, the temperature sensor may be arranged between an exhaust gas sampler and the particulate filter to provide a temperature indicative of the temperature in the area of the filter. In another embodiment, the temperature sensor may be arranged in the exhaust gas stream to provide a temperature indicative of the temperature of the sampled exhaust gas in the probe.

A controller is connected to the temperature sensor for processing the temperature signal and determining a filter temperature from the temperature signal. The controller commands the conditioning device in response to the filter temperature. In the first embodiment, the temperature sensor, controller, and conditioning device form a close loop system in which the conditioning device is continually adjusted based upon the temperature sensed in the area of the filter. In the second embodiment, the controller receives information from mass flow controllers or meters measuring the masses and temperatures of the dilution gas and diluted exhaust gas. The controller then calculates the temperature of the dilution air needed to obtain a desired temperature in the area of the filter based upon the measured temperature of the exhaust gas and information from the mass flow controllers or meters.

Accordingly, the present invention provides an active filter temperature control system and method enabling the temperature in the area of the filter to be maintained within a relatively tight range without adversely affecting the accuracy of the test.

BRIEF DESCRIPTION OF THE DRAWINGS

Other advantages of the present invention can be understood by reference to the following detailed description when considered in connection with the accompanying drawings wherein:

FIG. 2 is a schematic view of the present invention emissions sampling system utilizing the temperature of the exhaust gas and information from the mass flow controllers and meters; and FIG. 3 is a flow chart of the present invention method of actively controlling the filter temperature.

DETAILED DESCRIPTION OF THE PREFERRED EMBODIMENT

Figure 1:
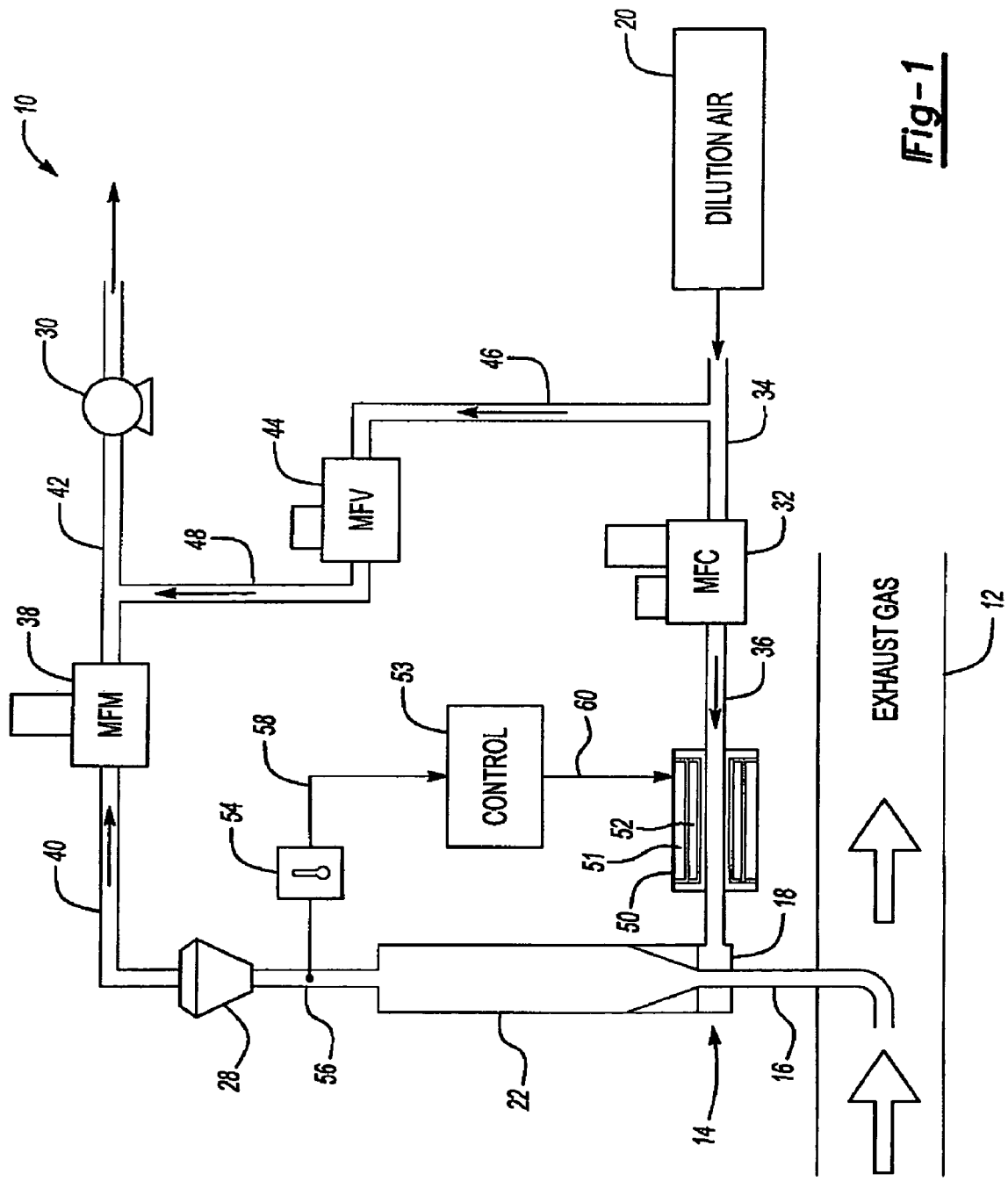
FIG. 1 is a schematic view of the present invention emissions sampling system with closed loop filter temperature feedback.

An emissions sampling system 10 is schematically shown in FIG. 1 suitable for measuring particulate matter from a vehicle engine or other power plant. A sampler 14 samples exhaust gas from an exhaust pipe 12 using a probe 16. The probe 16 collects a portion of the exhaust gas flowing through the pipe 12. A mixer 18 introduces a dilution gas such ambient air from a dilution gas source 20 to produce a diluted exhaust gas. The sampled exhaust gas and dilution air is homogeneously mixed in a dilution tunnel 22. Particulate matter within the diluted exhaust gas collects in a particulate filter 28. The diluted exhaust gas is drawn through filter 28 by a downstream blower 30 from which the diluted exhaust gas is vented to the atmosphere.

The flow of dilution air from the dilution gas source 20 is measured and controlled by a mass flow controller 32. Dilution air flows into the mass flow controller 32 from passage 34 and out passage 36 into the mixer 18. The diluted exhaust gas flows from the particulate filter 28 through passage 40 into mass flow meter 38 and out passage 42 through the blower 30. The mass flow meter 38 measures the mass of the diluted exhaust gas passing therethrough. The mass flow controller 32 and mass flow meter 38 are connected to the controller, which is not shown, to maintain a desired dilution ratio between the dilution air and the sampled exhaust gas throughout the test. In this manner, the total amount of particulate matter may be calculated from the sampled portion of exhaust gas, as is known in the art.

The mass flow controller 32 and mass flow meter 38 produce signals indicative of the mass and temperature of the fluid flowing therethrough. Although a mass flow controller 32 and a mass flow meter 38 are shown, it should be understood that other suitable devices may be used within the scope of the invention. A mass flow valve 44 is arranged between the passages 34 and 42. A passage 46 connects the passage 34 to the mass flow valve 44, and a passage 48 connects the mass flow valve 44 to the passage 42. The mass flow valve 44 controls the flow of dilution air to the passages downstream from the mass flow meter 38 and upstream of the blower 30 to adjust the flow of fluid through the blower 30 to maintain a desired volume of fluid flow through the system 10.

The present invention incorporates a conditioning device 50 preferably arranged between the dilution source 20 and the mixer 18. In this manner, diffusion losses may be avoided since exhaust gas is not carried in the dilution gas tubing. The conditioning device 50 may include both heating 51 and cooling 52 elements. In the embodiment shown in FIG. 1, the conditioning device 50 is connected to a controller 53 and a temperature sensor 54 that measures the temperature in the area of the particulate filter 28. Preferably, the temperature sensor 54 measures the temperature of the diluted exhaust gas in a passage 56 downstream from the dilution tunnel 22 before the particulate filter 28.

The temperature sensor 54 sends a temperature signal 58 to the controller 53. The controller 53 compares the temperature of the temperature sensor 54, which is indicative of the temperature in the area of the particulate filter 28, to determine whether adjustment of the dilution air temperature is required. The controller 53 may send a command signal 60 to the conditioning device 50 to either heat or cool the dilution air entering the mixer 18 to adjust the temperature of the diluted exhaust gas entering the particulate filter 28. The embodiment shown in FIG. 1 is a closed loop system in which the conditioning device is continually adjusted based upon the temperature sensed in the area of the particulate filter 28. The same controller 53 may also be connected to the mass flow controller 32, the mass flow meter 38, and the mass flow valve 44 for monitoring and controlling these devices.

FIG. 2 depicts another system in which the temperature of the diluted exhaust gas in the area of the particulate filter 28 is not controlled by the temperature sensed in that area, but rather, the temperature of the dilution air is adjusted depending upon the mass percent and temperature of the exhaust gas in the exhaust pipe 12. Using this method, it is necessary to account for the cooling that will occur in the tubing upstream of the mixing zone. Accordingly, the temperature of the probe ($T_{probe}$) is calculated from the temperature of the exhaust. The temperature of the exhaust is measured by a temperature sensor 62 arranged in the exhaust pipe 12. The relationship between the probe, dilution air, and diluted exhaust gas may be represented by the following equation:

$$m_{probe}T_{probe} + m_{dil}T_{dil} = m_{mix}T_{mix} \quad (1)$$

It follows that the temperature of the probe may be calculated by determined the following:

$$T_{probe} = \frac{m_{mix}T_{mix} - m_{dil}T_{dil}}{m_{probe}} \quad (2)$$

where, $$m_{probe} = m_{mix} - m_{dil} \quad (3)$$

Making the appropriate substitution, the temperature of the probe is:

$$T_{probe} = \frac{m_{mix}T_{mix} - m_{dil}T_{dil}}{m_{mix} - m_{dil}} \quad (4)$$

The temperature ($T_{mix}$) and mass percent ($m_{mix}$) of the diluted exhaust gas may be determined by information from the mass flow meter 38 represented by a signal 68, which is indicative of one or more signals including the mass percent ($m_{mix}$) of the diluted exhaust gas and the temperature ($T_{mix}$) of the diluted exhaust gas. Similarly, the mass percent ($m_{dil}$) and temperature ($T_{dil}$) of the dilution air may be determined from information provided by the mass flow controller 32, which is represented by the signal 66 indicative of one or more signals having the mass percent ($m_{dil}$) and temperature ($T_{dil}$) of the dilution air.

The controller 53 sends a command signal 70 to the conditioning device 50 to obtain a desired dilution air temperature sufficient to achieve the desired temperature in the area of the filter when mixed with an exhaust gas having the temperature sensed by the temperature sensor 62. This method does not use a closed loop control of filter temperature, but rather predicts the dilution air temperature needed to obtain the desired filter temperature. Said another way the filter temperature is determined based upon the exhaust temperature and a prediction of the required dilution air temperature to achieve a filter temperature within the desired range.

Referring to FIG. 3, the present invention method 72 is depicted in a flow chart form. A temperature is measured within the system 10, as indicated at block 74. The particulate filter temperature is determined by the controller 53 in block 76 either directly in a closed loop system, as indicated by the system in FIG. 1, or indirectly by a prediction, as indicated by the system in FIG. 2. The conditioning device 50 is commanded by the controller 53, as indicated by block 78, to raise or lower the dilution air temperature to achieve the desired filter temperature.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

What is claimed is:

1. An emissions sampling system comprising:
   an exhaust gas probe for sampling exhaust gas;
   a dilution gas source for providing dilution gas;
   a mixing device in fluid communication with said exhaust gas probe and said dilution gas source for mixing a sampled exhaust gas and the dilution gas to form a diluted exhaust gas;
   a particulate filter in fluid communication with said mixing device;
   a dilution temperature conditioning device arranged between said dilution gas source and said mixing device for obtaining a desired dilution gas temperature;
   a temperature sensor producing a temperature signal corresponding to a temperature of a fluid flowing through said sampling system; and
   a controller communicating with said temperature sensor and processing said temperature signal to determine a filter temperature from said temperature signal, said controller commanding said conditioning device in response to said filter temperature and a signal indicative of a mass of at least one of the sampled exhaust gas, the dilution and the diluted exhaust gas.

2. The sampling system according to claim 1, wherein said temperature is a diluted exhaust gas temperature indicative of said filter temperature.

3. The sampling system according to claim 2, wherein said temperature sensor is arranged between said mixing device and said particulate filter.

4. The sampling system according to claim 1, wherein said controller includes a desired filter temperature with said controller comparing said filter temperature to said desired filter temperature and commanding said conditioning device to obtain a desired dilution gas temperature calculated to achieve said desired filter temperature.

5. The sampling system according to claim 4, wherein said dilution temperature conditioning device includes a heating element and a cooling element.

6. The sampling system according to claim 4, wherein said desired filter temperature is in a range of 47° C. plus or minus 5°.

7. The sampling system according to claim 4, wherein said desired filter temperature is in a range of 25° C. plus or minus 5°.

8. The sampling system according to claim 4, wherein said desired dilution gas temperature is determined by said controller using the equation $$T_{probe} = \frac{m_{mix}T_{mix} - m_{dil}T_{dil}}{m_{probe}}.$$

$m_{probe}T_{probe} = m_{mix}T_{mix} - m_{dil}T_{dil}$, where $m_{mix}$ and $T_{mix}$ are signals indicative of the mass and temperature of the diluted exhaust gas, $m_{dil}$ and $T_{dil}$ are signals indicative of the mass and temperature of the dilution gas, and $m_{probe}$ and $T_{probe}$ are signals indicative of the mass and temperature of the sampled exhaust gas.

9. The sampling system according to claim 8, wherein said controller receives a dilution gas signals from a mass flow controller indicative of $m_{dil}$ and $T_{dil}$.

10. The sampling system according to claim 8, wherein said controller receives a diluted exhaust gas signal from a mass flow meter indicative of $m_{mix}$ and $T_{mix}$.

11. The sampling system according to claim 10, wherein said controller calculates the signal indicative of the mass of the sampled exhaust gas using the equation $m_{probe} = m_{mix} - m_{dil}$.

12. A method of controlling a particulate filter temperature in an emissions sampling system comprising the steps of:
   a) measuring a temperature of an exhaust sample into the system;
   b) determining the particulate filter temperature in response to performing step a) based upon a calculation using a signal indicative of a mass of the exhaust sample and the temperature;
   c) adjusting a dilution gas temperature in response to the filter temperature; and
   d) obtaining a desired particulate filter temperature in response to performing step c).

13. The method according to claim 12, wherein step b) includes determining the signal indicative of the mass using information from a mass flow meter.

14. An emissions sampling system comprising:
   an exhaust gas probe for sampling exhaust gas;
   a dilution gas source for providing dilution gas;
   a mixing device in fluid communication with said exhaust gas probe and said dilution gas source for mixing a sampled exhaust gas and the dilution gas to form a diluted exhaust gas;
   a particulate filter in fluid communication with said mixing device;
   a dilution temperature conditioning device arranged between said dilution gas source and said mixing device for obtaining a desired dilution gas temperature;
   a temperature sensor producing a temperature signal corresponding to a temperature of a fluid flowing through said sampling system;
   first and second mass determining devices respectively providing first and second mass signals indicative of masses of two of the dilution gas, the sampled exhaust gas and the diluted exhaust gas; and
   a controller communicating with said first and second mass determining devices and said temperature sensor, said controller processing said signals and determining a filter temperature, said controller commanding said conditioning device to a desired filter temperature in response to said filter temperature.

* * * * *

UNITED STATES PATENT AND TRADEMARK OFFICE
CERTIFICATE OF CORRECTION

PATENT NO. : 7,141,090 B2
APPLICATION NO. : 10/402282
DATED : November 28, 2006
INVENTOR(S) : Marek et al.

It is certified that error appears in the above-identified patent and that said Letters Patent is hereby corrected as shown below:

Claim 8, Column 5, lines 58-60: Delete " $$T_{probe} = \frac{m_{mix}T_{mix} - m_{dil}T_{dil}}{m_{probe}}$$ " after "equation"

Signed and Sealed this

Thirteenth Day of March, 2007

JON W. DUDAS
*Director of the United States Patent and Trademark Office*